United States Patent [19]

Davitz

[11] Patent Number: 4,948,557

[45] Date of Patent: * Aug. 14, 1990

[54] TARNISH RESISTANT GOLD COLORED ALLOY WITH ENHANCED GOLD COLOR

[76] Inventor: Daniel Davitz, 921 Harlem, Glenview, Ill. 60025

[*] Notice: The portion of the term of this patent subsequent to Jan. 23, 2007 has been disclaimed.

[21] Appl. No.: 304,874

[22] Filed: Feb. 1, 1989

Related U.S. Application Data

[63] Continuation-in-part of Ser. No. 294,774, Jan. 9, 1989, Pat. No. 4,895,701.

[51] Int. Cl.$^5$ .......................... C22C 30/02; C22C 5/08
[52] U.S. Cl. ..................................... 420/503; 420/502; 420/587
[58] Field of Search ..................... 420/503, 502, 587

[56] References Cited

U.S. PATENT DOCUMENTS

| | | | |
|---|---|---|---|
| 4,350,527 | 9/1982 | Davitz | 420/503 |
| 4,369,162 | 1/1983 | Wagner et al. | 420/503 |
| 4,804,517 | 2/1989 | Schaffer et al. | 420/580 |

*Primary Examiner*—Theodore Morris
*Assistant Examiner*—David W. Schumaker
*Attorney, Agent, or Firm*—Robert S. Beiser

[57] ABSTRACT

A gold colored, tarnish and corrosion resistant alloy is disclosed, usable for jewelry, dental purposes and the like. The alloy consists essentially of 24 to 27 percent palladium, 19 to 22 percent indium, 5 to 30 percent copper, 1 to 20 percent gold, and the balance is essentially silver.

9 Claims, No Drawings

TARNISH RESISTANT GOLD COLORED ALLOY WITH ENHANCED GOLD COLOR

BACKGROUND OF THE INvENTION

This application is a continuation-in-part of my prior co-pending application Ser. No. 294,774, filed Jan. 9, 1989, now U.S. Pat. No. 4,895,701.

The present invention provides an improved casting alloy for use in jewelry and dentistry. Gold is generally alloyed with other metals for such use and requires a relatively low melting point. The alloys must be moldable and castable with a low surface tension to permit conformance to intricate molds. Such alloys should provide a material which does not easily corrode or tarnish, especially when used in jewelry, or in the field of dentistry.

It is basic that gold is one of the most valuable metals and the look of gold is a highly desired characteristic of any metal alloy.

In accordance with this invention, an alloy is provided which contains no gold, and yet which provides an alloy material that polishes, works and looks like gold. Also the alloy of this invention can be corrosion resistant in the manner of gold in a liver sulfate atmosphere, or even in the presence of 30% chlorine solution. In the dental field, the preferred alloy of this invention may be finished in the manner of standard crown and bridge gold alloys.

The alloy of this invention may resemble 10 k gold in color and be highly corrosion resistant equal or superior to lower gold alloys, even though the alloy of this invention has zero percent gold.

In attempts of the prior art to develop a metal alloy possessing its true color of gold while maintaining its capabilities of being readily workable and polished, various non-precious metals and gold have been tried. For example, the present applicants' U.S. Pat. No. 4,350,527 is directed to a gold colored alloy having 0 to 10 percent gold content with 7 to 20 percent copper, 15 to 20 percent indium and 5 to 15 percent palladium. The alloy of '527 teaches 0 to 10 percent gold. However, '527 does not disclose the unexpected marked increase in gold color caused by the reaction of a copper and high indium content, combined with a high palladium content.

SUMMARY OF THE INVENTION

Accordingly, an object of the present invention is to provide a corrosion resistant and tarnish resistant alloy which simulates the color of gold colored alloys without the use of gold.

An additional object of the present invention is a metal alloy having chemical and physical properties suitable for use in jewelry and dentistry applications.

An additional object of the present invention is a metal alloy having enhanced tarnish and corrosion resistance provided by the use of a high concentration of palladium and indium while still maintaining a rich gold appearance.

Still a further object of the present invention is a gold colored metal alloy which is tarnish and corrosion resistant and has a rich gold appearance, with a markedly reduced cost due to the absence of gold content.

Other objects of the present invention and advantages accruing therefrom will be apparent to one skilled in the art in the following detailed description. All percentages referred to are percent by weight based on the total weight of the material or mixture then referred to.

DETAILED DESCRIPTION OF THE PREFERRED EMBODIMENT

In accordance with the present invention, a gold colored metal alloy is disclosed which is tarnish resistant and corrosion resistant and consists of the following ingredients: 20 to 27 percent palladium, 17 to 22 percent indium, 5 to 30 percent copper, with the remainder consisting essentially of silver. It is also desirable to add 0.25 to 1.00 percent ruthenium as a grain growth inhibitor. The alloys in accordance with the subject invention are a rich gold color which approximates a 10 carat alloy. In addition, tarnish resistance and corrosion resistance are greatly increased.

As mentioned above, in the present alloy, no gold is present. Despite the zero percent gold content, the alloy possesses a rich gold color and maintains a high tarnish resistance, even in the presence of a high percentage of copper. It is known that without a high percentage by weight of indium and a lower silver content, the alloy would appear white (silver color), but a higher percentage of indium in the presence of gold turns the alloy yellow. Ordinarily, the higher the gold content, the less silver is required to obtain a rich gold color. The preferred alloy of the present invention contains no gold, yet possesses a rich gold color. This is believed to occur from a high percentage of indium and palladium in the presence of copper, the combination of which causes the unexpectedly marked increase in gold color, even where no gold is present. It is believed that this result occurs because the indium and copper combine to produce a rich gold color, and which mixture surrounds the granules thereby preserving the rich gold color. A deviation of the indium and palladium will cause a lighter gold color. For example, dropping the indium and palladium content below the range specified herein will produce a very light color, which is silver in appearance.

Palladium strongly inhibits the tarnishing of this alloy. Although 20 to 26 percent of palladium is acceptable for this invention, 25.5% was found to be optimal in the presence of 21% indium.

It would normally be expected that palladium in concentrations above 11 percent by weight, would cause the gold color of this invention to become diluted, as reported in U.S. Pat. No. 4,350,527. Generally, the higher above an 11 percent concentration of palladium, the more diluted the gold color becomes. However, it was unexpectedly found that a much higher concentration of palladium in the presence of copper and a high indium concentration, actually creates a deeper gold color than would be expected from an alloy having palladium in concentration of approximately 10 percent.

While from 17 to 22 percent of indium may be present in the alloy, it is preferred that 21 percent of the indium is present. In lower concentrations the gold color of the alloy of this invention may be diluted. The indium also provides flowability to the material and displays a notable reflective characteristic.

It is desirable to have a minimum of at least 5 percent copper present to combine with the indium to create the gold colored appearance of the alloy. As stated earlier, 5 to 30 percent copper may be present, however 18 percent is preferred for increased tarnish resistance.

It would normally be expected that copper, at concentrations in excess of 17 percent by weight would diminish the tarnish resistance of the alloy. However, in the presence of a high percentage of palladium the opposite result was found to occur. The resulting alloy exhibits a metal alloy possessing a rich gold color with excellent tarnish and corrosion resistant properties.

It is generally preferred that the balance of the alloy of this invention be comprised of silver, to provide an alloy which looks and behaves like gold while exhibiting a greatly reduced cost.

In an alternative embodiment, gold may be added in concentrations ranging from 1 to 20 percent. Although the cost of this alternative alloy would not be as greatly reduced, the gold color could be enhanced to mimic a 14 carat alloy and the tarnish and corrosion resistance would be much higher.

The casting temperature of the present invention described is approximately 2150 degrees Farenheit ±50 and the melting temperature is approximately 1700 degrees Farenheit ±50. Such temperatures are sufficiently low to permit the formation of a melt and easy casting. Ruthenium is preferably added to the alloy to prevent grain growth. The specific gravity of the preferred alloy is approximately 8.65 grams/cubic centimeter plus or minus 0.5. Other physical properties of the alloy of the present invention are approximately as follows:

| Low hardness | 160 |
|---|---|
| High hardness | 227 |
| Elongation | 3–6% |

Specifically, the preferred alloy formula in accordance with this invention is:

| Palladium | 25.5% |
|---|---|
| Indium | 21.0% |
| Copper | 18.0% |
| Silver | 34.95% |
| Ruthenium | .05% |

In an alternative embodiment, the alloy formula in accordance with this invention is:

| Palladium | 25.5% |
|---|---|
| Indium | 21.0% |
| Copper | 18.0% |
| Gold | 10.0% |
| Silver | 24.95% |
| Ruthenium | .05% |

Because of the presence of cooper or palladium in the percentages of this invention, the alloy becomes highly tarnish resistant in a liver sulfate atmosphere and a solution of 30% chlorine and H$_2$O.

While the invention has been described with reference to a preferred content and formula, it will be understood by those skilled in the art that various changes may be made and equivalents substituted for elements described herein without departing from the scope of the invention. In addition, many modifications may be made to adapt to a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

I claim as my invention:

1. A gold colored, highly tarnish and corrosion resistant alloy which consists essentially of, by weight, 17 to 22 percent indium, 24 to 27 percent palladium, 5 to 30 percent copper, 1 to 20 percent gold, and the balance consisting essentially of silver.

2. The alloy of claim 1, having a casting temperature of approximately 2150 degrees F. ±50 degrees F.

3. The alloy of claim 1, having a melting temperature of approximately 1700 degrees F. ±50 F.

4. The alloy of claim 1 in which said balance of silver does not exceed 47 percent.

5. A dental alloy suitable for crown, bridges, and other dental apparatus which consists essentially of a gold colored, highly tarnish resistant and corrosion resistant alloy comprising, by weight, approximately 18 percent copper, approximately 21 percent indium, approximately 25.5 percent palladium, approximately 10 percent gold and the balance silver.

6. An article of jewelry made of an alloy consisting essentially, by weight, approximately 18 percent copper, approximately 21 percent indium, approximately 25.5 percent palladium, approximately 10 percent gold, and the balance is silver.

7. An article of jewelry formed of the alloy of claim 1.

8. The alloy of claim 1, wherein said alloy has a specific gravity of 8.65 grams per cubic centimeter plus or minus 0.5.

9. The alloy of claim 1, wherein 0.25 to 1.0 weight percent of ruthenium is present to serve as a grain growth inhibitor.

* * * * *